US 9,517,314 B2

(12) United States Patent
Hately et al.

(10) Patent No.: US 9,517,314 B2
(45) Date of Patent: Dec. 13, 2016

(54) DOSE INDICATOR DEVICE (71) Applicant: CONSORT MEDICAL PLC, Hemel Hempstead (GB)

(72) Inventors: Graham Hately, Norfolk (GB); Richard Warby, Cambridgeshire (GB)

(73) Assignee: CONSORT MEDICAL PLC, Hemel Hempstead (GB)

(*) Notice: Subject to any disclaimer, the term of this patent is extended or adjusted under 35 U.S.C. 154(b) by 289 days.

(21) Appl. No.: 14/118,148

(22) PCT Filed: May 31, 2013

(86) PCT No.: PCT/GB2013/051459
§ 371 (c)(1),
(2) Date: Nov. 15, 2013

(87) PCT Pub. No.: WO2013/182843
PCT Pub. Date: Dec. 12, 2013

(65) Prior Publication Data
US 2015/0217066 A1 Aug. 6, 2015

(30) Foreign Application Priority Data

Jun. 6, 2012 (GB) .................................. 1209995.8

(51) Int. Cl.
A61M 15/00 (2006.01)
G06M 1/02 (2006.01)
(Continued)

(52) U.S. Cl.
CPC ....... *A61M 15/0071* (2014.02); *A61M 15/009* (2013.01); *A61M 15/0021* (2014.02);
(Continued)

(58) Field of Classification Search
CPC .............. A61M 15/00; A61M 15/0001; A61M 15/0065; A61M 15/0068; A61M 15/007; A61M 15/0071; A61M 15/0073; A61M 15/0075; A61M 15/0076; A61M 15/0081; A61M 15/009; A61M 15/08; G06M 1/041–1/083; G06M 1/163; G06M 1/24–1/26
(Continued)

(56) References Cited

U.S. PATENT DOCUMENTS 4,445,404 A 5/1984 Parker
5,482,030 A 1/1996 Klein
(Continued)

FOREIGN PATENT DOCUMENTS

CN 1826609 A 8/2006
CN 101808687 A 8/2010
(Continued)

OTHER PUBLICATIONS

Examination Report dated Nov. 25, 2014 from the European Patent Office for European Application (13 726 847.0).
(Continued)

*Primary Examiner* — Tan-Uyen (Jackie) T Ho
*Assistant Examiner* — Joseph D Boecker
(74) *Attorney, Agent, or Firm* — Smith, Gambrell & Russell, LLP (57) ABSTRACT A dose indicator device for a pressurized metered dose inhaler comprises an inner wheel, annular outer wheel, actuator and housing;
the inner wheel comprising primary indexing teeth and a flexible drive arm;
the outer wheel comprising secondary indexing teeth on an outer face of the outer wheel;
the inner wheel and outer wheel located at least partially within the housing such that the inner wheel and outer wheel are rotatable about a common longitudinal axis of rotation;

(Continued)

the actuator movable in a plane perpendicular to the axis of rotation to engage the primary indexing teeth to rotate the inner wheel;
the housing being fixed relative to the axis of rotation and comprising a deflector;
the deflector configured such that, on rotation of the inner wheel, the drive arm is intermittently deflected and brought into contact with the secondary indexing teeth to rotate the outer wheel about the axis of rotation.

25 Claims, 11 Drawing Sheets

(51) Int. Cl.
*G06M 1/04* (2006.01)
*G06M 1/16* (2006.01)

(52) U.S. Cl.
CPC .......... *A61M 15/0075* (2014.02); *G06M 1/02* (2013.01); *G06M 1/045* (2013.01); *G06M 1/166* (2013.01)

(58) Field of Classification Search
USPC ............. 128/200.14, 200.23, 203.15, 205.23
See application file for complete search history.

(56) References Cited

U.S. PATENT DOCUMENTS

| | | | |
|---|---|---|---|
| 5,485,971 A | 1/1996 | Nakaya et al. | |
| 5,489,143 A | 2/1996 | Adachi et al. | |
| 5,490,749 A | 2/1996 | Arbues | |
| 5,794,978 A | 8/1998 | Nishide | |
| 5,988,496 A * | 11/1999 | Bruna | G06M 1/041 222/18 |
| 6,070,502 A | 6/2000 | Chang | |
| 6,161,724 A | 12/2000 | Blacker et al. | |
| 6,175,994 B1 | 1/2001 | Nicoletti | |
| 6,234,168 B1 | 5/2001 | Bruna | |
| 6,267,315 B1 | 7/2001 | Blackadder et al. | |
| 6,283,365 B1 * | 9/2001 | Bason | G06M 1/041 235/116 |
| 6,446,627 B1 | 9/2002 | Bowmen et al. | |
| 6,481,438 B1 * | 11/2002 | Gallem | A61M 15/009 128/200.14 |
| 6,659,307 B1 * | 12/2003 | Stradella | A61M 15/009 116/278 |
| 7,100,530 B2 | 9/2006 | Lu | |
| 7,137,391 B2 | 11/2006 | Bruna | |
| 7,252,065 B1 | 8/2007 | Keeton | |
| 7,584,712 B2 | 9/2009 | Lu | |
| 7,621,273 B2 | 11/2009 | Morton et al. | |
| 7,650,883 B2 | 1/2010 | Scarrott et al. | |
| 7,780,038 B2 | 8/2010 | Ingram et al. | |
| 7,793,798 B2 | 9/2010 | Stradella et al. | |
| 7,806,295 B2 * | 10/2010 | Stradella | A61M 15/009 128/205.23 |
| 7,882,982 B2 | 2/2011 | Stradella et al. | |
| 8,074,594 B2 | 12/2011 | Lu | |
| 8,113,199 B2 | 2/2012 | Augustyn et al. | |
| 8,132,712 B2 | 3/2012 | Fenlon | |
| 8,245,906 B2 | 8/2012 | Crosby et al. | |
| 8,348,095 B2 | 1/2013 | Laut et al. | |
| 8,944,053 B2 | 2/2015 | Laut | |
| 9,053,415 B2 | 6/2015 | Le Jeune et al. | |
| 2005/0011515 A1 * | 1/2005 | Lee | A61M 15/009 128/200.23 |
| 2010/0192946 A1 * | 8/2010 | Oi | A61M 15/009 128/200.23 |
| 2010/0258121 A1 | 10/2010 | Kirniak | |
| 2011/0220450 A1 | 9/2011 | Chiang | |
| 2012/0012612 A1 * | 1/2012 | Laut | G06M 1/041 222/36 |
| 2012/0090607 A1 * | 4/2012 | Le Jeune | G06M 1/04 128/203.15 |
| 2012/0103331 A1 * | 5/2012 | Laut | G06M 1/248 128/203.15 |
| 2012/0111323 A1 | 5/2012 | Bacon et al. | |
| 2015/0101599 A1 * | 4/2015 | Berry | A61M 15/009 128/202.22 |

FOREIGN PATENT DOCUMENTS

| | | | | |
|---|---|---|---|---|
| CN | 102460485 A | 5/2012 | | |
| EP | 0480488 B1 | 4/1992 | | |
| EP | 0 949 584 A2 | 10/1999 | | |
| EP | 0 966 309 B1 | 6/2004 | | |
| EP | 1758631 A1 | 3/2007 | | |
| FR | 2 940 642 A1 | 7/2010 | | |
| GB | 2191032 A | 12/1987 | | |
| SE | WO 0137909 A1 * | 5/2001 | ........ | A61M 15/0065 |
| WO | 98/01822 A1 | 1/1998 | | |
| WO | 98/28033 A2 | 7/1998 | | |
| WO | 01/31578 | 5/2001 | | |
| WO | 01/37909 A1 | 5/2001 | | |
| WO | 01/87391 | 11/2001 | | |
| WO | 03/028791 A1 | 4/2003 | | |
| WO | 2005/114563 A1 | 12/2005 | | |
| WO | 2008/119552 A1 | 10/2008 | | |
| WO | 2009/103711 | 8/2009 | | |
| WO | 2010/103315 A2 | 9/2010 | | |

OTHER PUBLICATIONS

Combined Search and Examination Report issued by The Great Britain Intellectual Property Office in family member application No. GB120995.8, dated Sep. 27, 2012.
International Search Report for PCT/GB2013/051459 mailed Sep. 26, 2013.
International Preliminary Report on Patentability for PCT/GB2013/051459 dated Dec. 9, 2014 (7 pages).
Written Opinion of the International Searching Authority for PCT/GB2013/051459 dated Dec. 6, 2014 (6 pages).
First Notification of Office Action and Search Report in Chinese Patent Application No. 201380030039.1, dated Jun. 3, 2016, 9 pages.
European Search Report dated Sep. 30, 2016 in corresponding European Patent Application No. EP 16 16 8625.

* cited by examiner

DOSE INDICATOR DEVICE

The present disclosure relates to a dose indicator device and apparatus comprising such devices, and in particular to a dose indicator device for use with, or incorporated as part of a pressurised metered dose inhaler.

BACKGROUND

It has been recognised that there is a need to provide accurate information to a user of a dispensing apparatus, such as a pressurised metered dose inhaler, concerning the quantity of doses delivered from, or remaining in, the dispensing apparatus. Without such information, there is a danger that a user may be unaware that the dispensing container of the dispensing apparatus is empty or close to empty. This is especially dangerous where the dispensing apparatus is for use in delivering medicinal compounds for the treatment of chronic or acute symptoms, for example, as in the case of a pressurised metered dose inhaler used for treating asthmatic reactions.

It is known to provide a dispensing apparatus with a dose indicator device. Typically such dose indicator devices are triggered by movement of the dispensing container wherein the movement either directly or indirectly provides the motive force for incrementing or decrementing the dose indicator device. EP1758631 disclose one example of a dose indicator device. This device, while accurate and robust, comprises a relatively large number of separate components.

It would be desirable to produce a dose indicator device that requires fewer components.

SUMMARY OF THE DISCLOSURE

According to the present disclosure there is provided a dose indicator device for a pressurised metered dose inhaler comprising:

an inner wheel, an annular outer wheel, an actuator and a housing;

the inner wheel comprising a plurality of primary indexing teeth and a flexible drive arm;

the annular outer wheel comprising a plurality of secondary indexing teeth on an outer face of the annular outer wheel;

the inner wheel and outer annular wheel being located at least partially within the housing such that the inner wheel and annular outer wheel are rotatable about a common longitudinal axis of rotation;

the actuator being movable in a plane perpendicular to the longitudinal axis of rotation to engage the primary indexing teeth of the inner wheel to rotate the inner wheel;

the housing being fixed relative to the longitudinal axis of rotation and comprising a deflector;

the deflector being configured such that, on rotation of the inner wheel, the flexible drive arm is intermittently deflected by the deflector and is thereby brought into contact with the secondary indexing teeth so as to rotate the annular outer wheel about the axis of rotation.

Advantageously, the dose indicator device comprises a relatively small number of separate components and is suitable to form a compact, space-saving design.

The inner wheel may be cylindrical in shape and may be solid or may be provided with a central bore. The inner wheel may have a stepped diameter with portions of different diameter.

The annular outer wheel may have the form of a ring and may be circular in shape.

The inner wheel may be at least partially nested within the longitudinal extent of the annular outer wheel. By arranging the inner wheel at least partly within the annular outer wheel the 'depth' of the dose indicator device measured in a direction along the longitudinal axis of rotation may be minimised, since it is not necessary to stack the two wheels one upon the other.

The deflector may be configured such that, on rotation of the inner wheel, the flexible drive arm is intermittently deflected by the deflector inwardly towards the longitudinal axis.

In one aspect a proximal end of the flexible drive arm of the inner wheel may be located closer to the longitudinal axis than the secondary indexing teeth and a distal end of the flexible drive arm may be located further from the longitudinal axis than the secondary indexing teeth when not in contact with the deflector. Thus, the flexible drive arm is enabled to engage the secondary indexing teeth on the outer face of the annular outer wheel.

The housing may further comprise a first flexible restraint which engages the inner wheel to restrain rotation of the inner wheel when not being rotated by the actuator and a second flexible restraint which engages the annular outer wheel to restrain rotation of the annular outer wheel when not being rotated by the inner wheel.

The restraints advantageously serve to restrain movement of the inner wheel and annular outer wheel other than when the wheels are being positively driven during a counting action. This helps to minimise the chances of the dose indicator device changing the displayed indication if the device is dropped, shaken or otherwise knocked.

The inner wheel may comprise a plurality of indentations on an outer face of the inner wheel which are engagable by the first flexible restraint. The plurality of indentations may be located circumferentially around the inner wheel with the primary indexing teeth located to one side of the plurality of indentations. The indentations may have a cross-sectional shape that is part-circular or otherwise smoothly curved and the portion of the first flexible restraint that engages the indentations may have a matching circular shape.

The second flexible restraint may be engagable with the secondary indexing teeth of the annular outer wheel. The secondary indexing teeth may have a cross-sectional shape that is part-circular or otherwise smoothly curved and the portion of the second flexible restraint that engages the secondary indexing teeth may have a matching circular shape.

The housing may comprise a mounting aperture for the inner wheel enabling the inner wheel to rotate therein relative to the housing. Advantageously the housing may function to mount and locate the annular outer wheel and the inner wheel relative to one another while allowing both wheels to rotate.

In one aspect the inner wheel may comprise a plurality of indentations on an outer face of the inner wheel which are engagable by the first flexible restraint and wherein the plurality of indentations form the bearing surface of the inner wheel in the mounting aperture. In this aspect, a portion of a boundary of the mounting aperture may comprise a first flexible restraint which is engagable with the plurality of indentations of the inner wheel to restrain rotation of the inner wheel when not being rotated by the actuator.

In one aspect the actuator may be provided on an actuator member, said actuator member being movable by a dispensing container of a pressurised metered dose inhaler into an indexing position on actuation of the pressurised metered dose inhaler to engage the actuator with the primary indexing teeth of the inner wheel to rotate the inner wheel; wherein said actuator member may be biased away from the indexing position such that the actuator is disengaged from the primary indexing teeth when the pressurised metered dose inhaler is in a non-dispensing position.

The actuator member may take the form of a plunger or carriage which is slidable relative to an actuator housing of the pressurised metered dose inhaler. The actuator member may comprise a head part that in use is contacted by a part of the dispensing container of the pressurised metered dose inhaler (such as the valve ferrule), a stem part that movably mounts the actuator member to the housing of the pressurised dispensing container and the actuator itself which may be in the form of a flexible arm. The actuator member may comprise an aperture into or through which a portion of the inner wheel extends so as to locate the primary indexing teeth in alignment with the actuator. Again, this allows for a more compact arrangement of the components. The biasing of the actuator member may be achieved by providing a compression spring between the stem part and the actuator housing or by integrating a flexible, sprung leg into the actuator member that is compressed and strained during actuation of the pressurised metered dose inhaler. In one aspect, the head part of the actuator member comprises an annular yoke through which on assembly a valve stem of the pressurised dispensing container projects. In this aspect the stem part may comprise a carriage that slides within a C-section channel provided on the actuator housing. The stem part may comprise at least one downwardly extending leg on which is provided the flexible arm actuator. The C-section channel comprises the aperture allowing the inner wheel to project therethrough.

The intermittent engagement of the one or more secondary indexing teeth of the inner wheel and the indexing teeth of the annular outer wheel serve to enable the annular outer wheel to be incremented only after a plurality of rotational increments of the inner wheel. For example, the inner wheel and the annular outer wheel may have a gear ratio such that for every 10 incremental rotations of the inner wheel the annular outer wheel is incrementally rotated once. Consequently, for every 10 actuations of the inner wheel by the actuator the inner wheel will rotate through 360° and the flexible drive arm of the inner wheel will be deflected to engage the secondary indexing teeth of the annular outer wheel once to rotate it one increment. In another example, a gear ratio of 10:1 can be achieved by providing two flexible drive arms on the inner wheel at 180° spacing, two deflectors on the housing at 180° spacing and 20 primary indexing teeth. Other gear ratios can be used as desired. For example, the annular outer wheel can be arranged to incrementally rotate every 20 actuations of the pressurised dispensing container by providing one flexible drive arm and 20 primary indexing teeth on the inner wheel.

The housing may comprise a first housing part which is engagable with a wall portion of an actuator housing of a pressurised metered dose inhaler to define a housing enclosure containing the inner wheel and annular outer wheel. Advantageously, the components of the dose indicator device are kept in correct alignment by being held between the housing of the dose indicator device and the actuator housing which therefore requires fewer components than needed for a dose indicator housing that itself fully defines the housing enclosure.

The first housing part may comprise the deflector.

The inner wheel and/or annular outer wheel may comprise dosage indicia. The dosage indicia may be in the form of numbers, words, letters, colours, pictograms or similar. For example a decreasing series of numbers can be displayed: 200, 190, 180, 170, etc. where a gear ratio of 10:1 is used between the inner wheel and the outer annular wheel. Alternatively, where it is not desired to show a numerical count but simply to indicate to a user that the end of the useful life of the pressurised metered dose inhaler is approaching, the indicia could be in the form of a changing colour, e.g. a display that changes from green, through orange to red, or in the form of words which are displayed near or at the end of the pack life such as "Order replacement now" and "Empty".

Dosage indicia may be presented only on the annular outer wheel where individual dosage counts are not to be displayed to a user. Alternatively, the inner wheel may also be provided with dosage indicia where individual dosage counts are desired to be displayed.

The dosage indicia may be provided on an end face of the inner wheel and/or outer wheel, the end faces being perpendicular to the longitudinal axis.

The present disclosure also relates to a pressurised metered dose inhaler comprising an actuator housing, a pressurised dispensing container received in the actuator housing and a dose indicator device as described in any of the aspects above.

The pressurised metered dose inhaler may comprise a housing enclosure containing the inner wheel and annular outer wheel, the housing enclosure being defined by a first housing part of the dose indicator device and a wall portion of the actuator housing.

The wall portion may comprises a rear wall of the actuator housing such that the housing enclosure is located between a stem block and the rear wall of the actuator housing. Advantageously, positioning the dose indicator to the rear of the stem block permits a clear airway to be provided between the stem block and the front of the actuator housing.

In one embodiment, the actuator housing may be formed from two mouldings, comprising a front case and a rear case. The front case may comprise the dispensing orifice (mouthpiece or nasal piece for example). The actuator housing may have a split line between the front and rear cases that runs down the length of the actuator housing to split the compartment receiving the pressurised dispensing container in two. The front and rear cases may be joined by a snap-fit arrangement.

In an alternative embodiment, the actuator housing may be formed from two mouldings, comprising a top case and a bottom case. The bottom case may comprise the dispensing orifice (mouthpiece or nasal piece for example). The top and bottom cases may be joined by a snap-fit arrangement.

The pressurised metered dose inhaler may further comprise a window in the actuator housing for viewing the inner wheel and/or outer wheel therethrough.

The window may be sized so as only to show the annular outer wheel and to obscure view of the inner wheel. Alternatively both wheels may be visible.

The components of the dose indicator device and actuator housing are preferably formed from plastics mouldings, except for the compression spring (when present) which may be metal or plastic.

Rigid components of the dose indicator device may be formed from, for example, polyester, nylon, polypropylene, polyacetal, ABS or similar.

Preferably, the flexible drive arm, flexible restraints and the actuator drive arm are formed from an elastic material such that imparted strains during normal actuation are recoverable elastically. A suitable example is polyacetal (POM).

The dose indicator device may be used with, or form a part of a pharmaceutical dispensing device, such as, for example, a pulmonary, nasal, or sub-lingual delivery device. A preferred use of the dose indicator device is with a pharmaceutical pressurised metered dose aerosol inhaler device. The term pharmaceutical, as used herein, is intended to encompass any pharmaceutical, compound, composition, medicament, agent or product which can be delivered or administered to a human being or animal, for example pharmaceuticals, drugs, biological and medicinal products. Examples include antiallergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bicarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2 isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and di-methyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

BRIEF SUMMARY OF THE DRAWINGS

Embodiments of the present disclosure will now be described, by way of example, with reference to the accompanying drawings, in which:—

DETAILED DESCRIPTION

Figure 1:
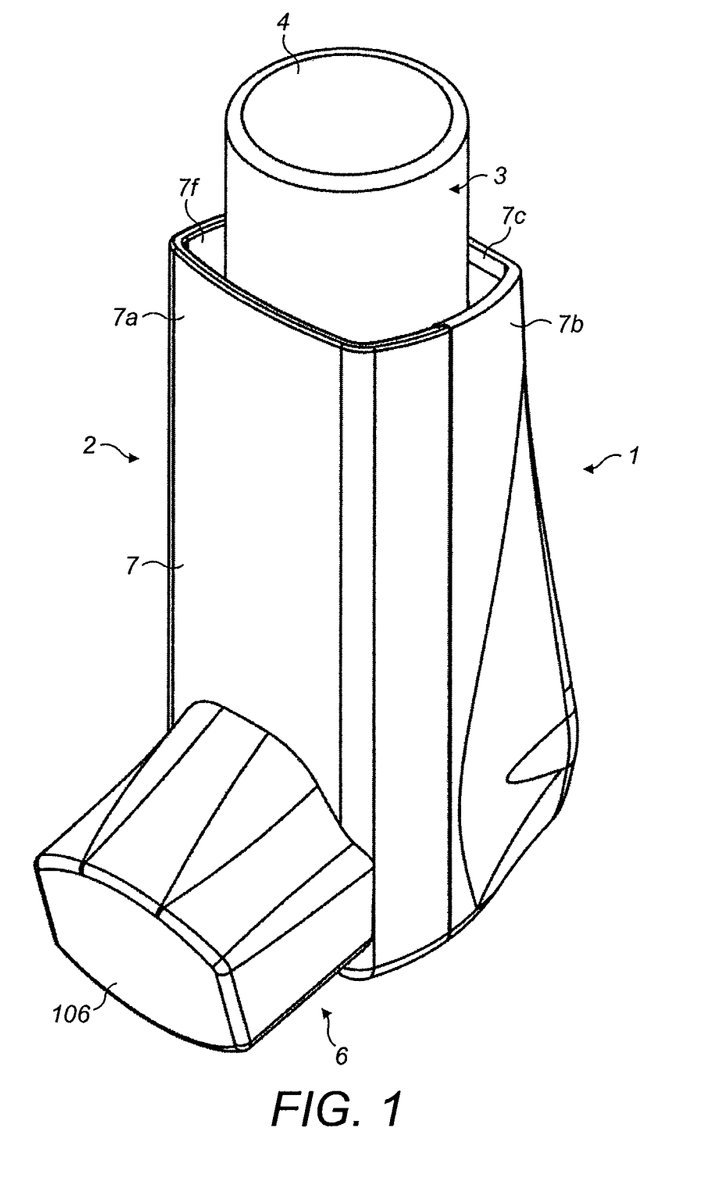
FIG. 1 is a perspective view of a pressurised metered dose inhaler comprising a dose indicator device according to the present disclosure and including a pressurised dispensing container.

FIG. 1 shows a pressurised metered dose inhaler 1 which comprises an actuator housing 2 that contains a pressurised dispensing container 3.

Figure 4:
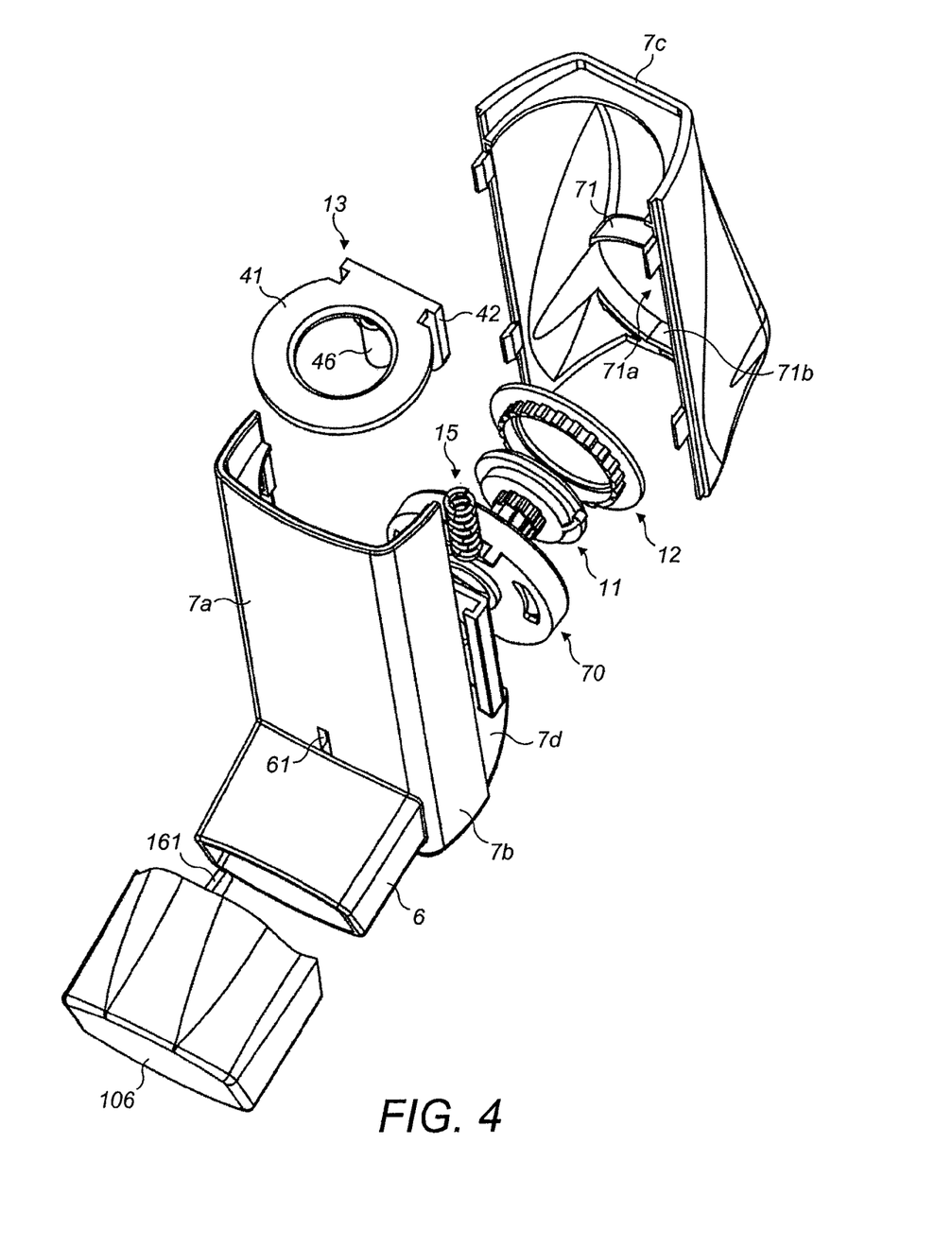
FIG. 4 is an exploded perspective view of the pressurised dispensing container of FIG. 1 from another angle.

The actuator housing 2 comprises a generally tubular body 7 and a depending mouthpiece 6 at one end covered by a dust cap 106. The tubular body 7 may have a generally circular cross-sectional shape. However, in the illustrated example the tubular body 7 comprises a squarer cross-sectional shape with a front wall 7a, side walls 7b and rear wall 7c. A stem block 8 is provided at a basal end of the tubular body 7 nearest the mouthpiece 6. The actuator housing 2 may be formed from two mouldings comprising a front case 17a and a rear case 17b. The front case 17a comprises the mouthpiece 6 and a portion of the tubular body 7 comprising the front wall 7a and half of each side wall 7b. In addition; the front case 17a comprises a base 7d of the actuator housing 2 from which project the stem block 8, a C-section channel 8 and a tubular extension 10 defining a bore. The C-section channel 80 comprises an aperture 81. The rear case 17b comprises the rear wall 7c and the remainder of the side walls 7b. A rim 71 provided on an inner face of the rear case 17b, as shown in FIG. 4, defines a cavity 71a the function of which will be described below. The rim 71 is generally circular except for a flattened section 71a. The front and rear cases 17a, 17b may be snap-fit together by means of formations 7e on each casing. A viewing window 62 in the form of a cut out is provided in the rear wall 7c of the actuator housing 2. A lock-out aperture 61 is provided in the front wall 7a just above the mouthpiece 6. The dust cap 106 is provided with a body that encloses the mouthpiece 6 and a tang 161 that in use can protrude through the lock-out aperture 61 when the dust cap 106 is in position on the mouthpiece 6.

The pressurised dispensing container 3 typically comprises a canister 4 and a valve (not shown). To assemble the pressurised metered dose inhaler, the dispensing container 3 is inserted into an open end 7f of the tubular body 7 of the housing 2 such that a valve stem of the valve is received in the stem block 8.

According to the present disclosure, the pressurised metered dose inhaler 1 includes a dose indicator device marked generally by reference 9. The dose indicator device is located towards the mouthpiece end of the tubular body 7 situated between the stem block 8 and the rear wall 7c.

Figure 2:
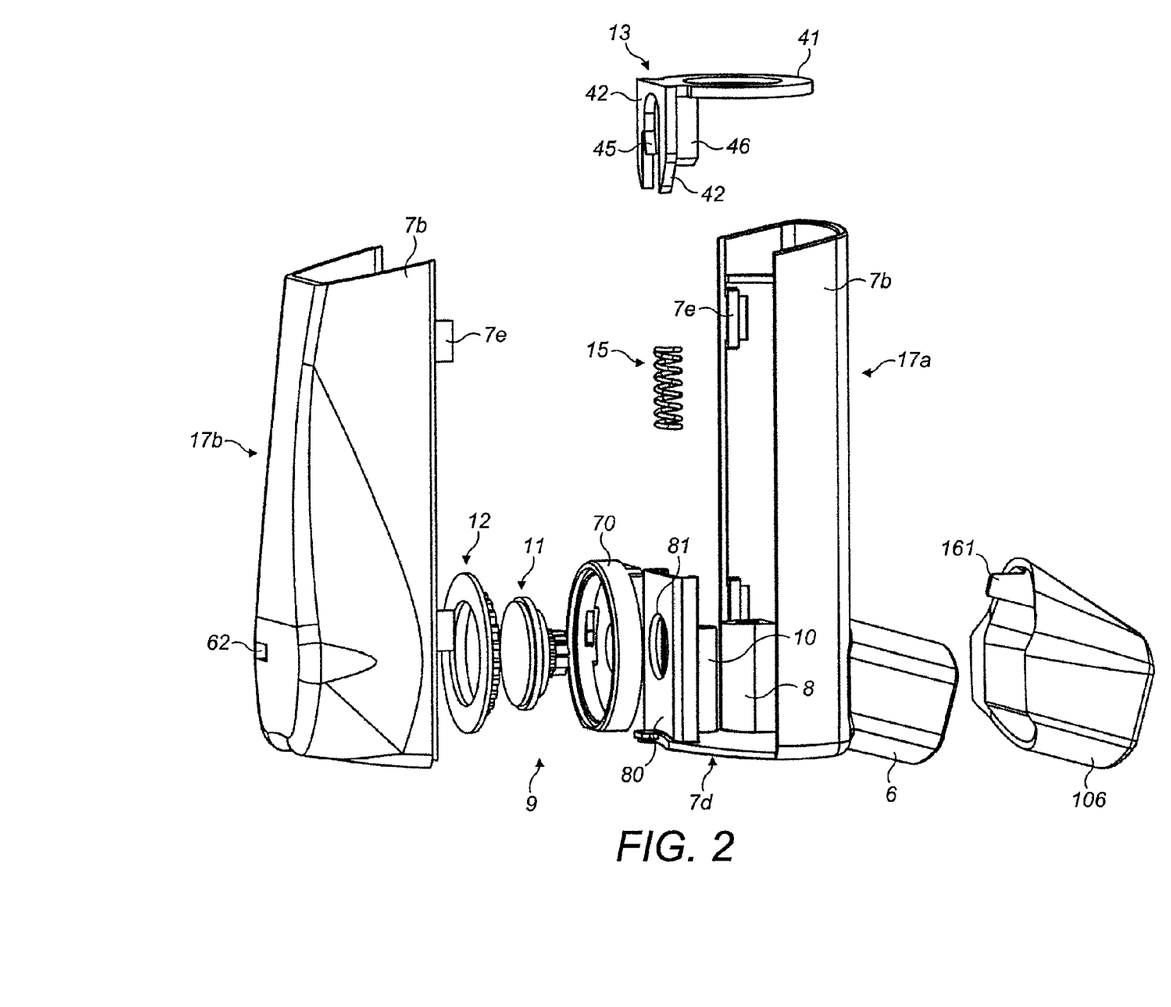
FIG. 2 is an exploded perspective view of the pressurised metered dose inhaler of FIG. 1.

In general the dose indicator device 9 comprises an inner wheel 11, an annular outer wheel 12, an actuator member 13, a cup-shaped housing 70 and a spring 15. The cup-shaped housing 70 of the dose indicator device 9 defines, together with the rear wall 7c, a housing enclosure of the dose indicator device 9 which locates and aligns the inner wheel 11 and annular outer wheel 12.

In the following description, unless the context otherwise requires, the term "inwardly-facing" refers to a direction which is inwards towards the pressurised dispensing container 3 within the tubular body 7. The term "outwardly-facing" refers to a direction which is outwards away from the pressurised dispensing container 3 within the tubular body 7. Further, unless the context otherwise requires, terms such as "upwards" refer to the direction towards the open end 7f of the tubular body 7 while terms such as "downwards" refer to the opposite direction.

Figure 5:
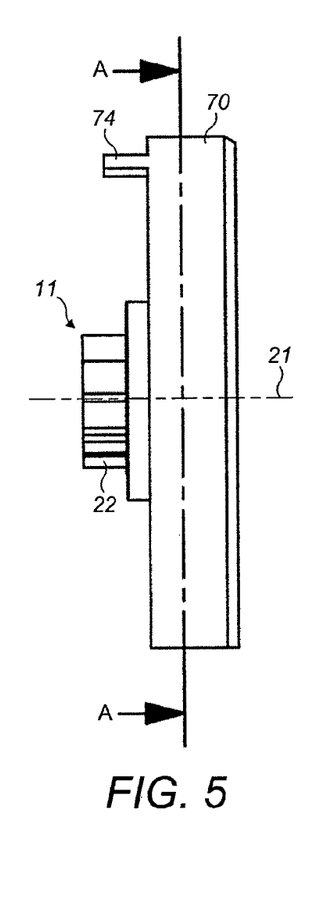
FIG. 5 is a side elevation of a portion of a dose indicator device according to the present disclosure.

The inner wheel 11 comprises a generally solid cylindrical body 20 that is mounted in use to rotate about a first rotational axis 21 as marked on FIG. 5. The body 20 is provided with three layers which are positioned adjacent to one another in a direction along the first rotational axis 21. The first layer comprises a plurality of primary indexing teeth 22. In the example shown there are 10 primary indexing teeth 22. Adjacent the primary indexing teeth 22 is the second layer which comprises a plurality of indentations 24. Each indentation 24 takes the form of a part circular cut out in the body 20 of the inner wheel 11. In the example shown there are 10 indentations 24, 1 for each of the primary indexing teeth 22. Adjacent the indentations 24 is the third layer which comprises a flexible drive arm 23. The flexible drive arm 23 comprises an arm portion 23a that depends from the body 20 and terminates at a distal end with a circular pin 23b. As shown most clearly in FIG. 9, an end face 20a of the body 20 of the inner wheel 11 comprises a peripheral rebate 25.

Figure 8:
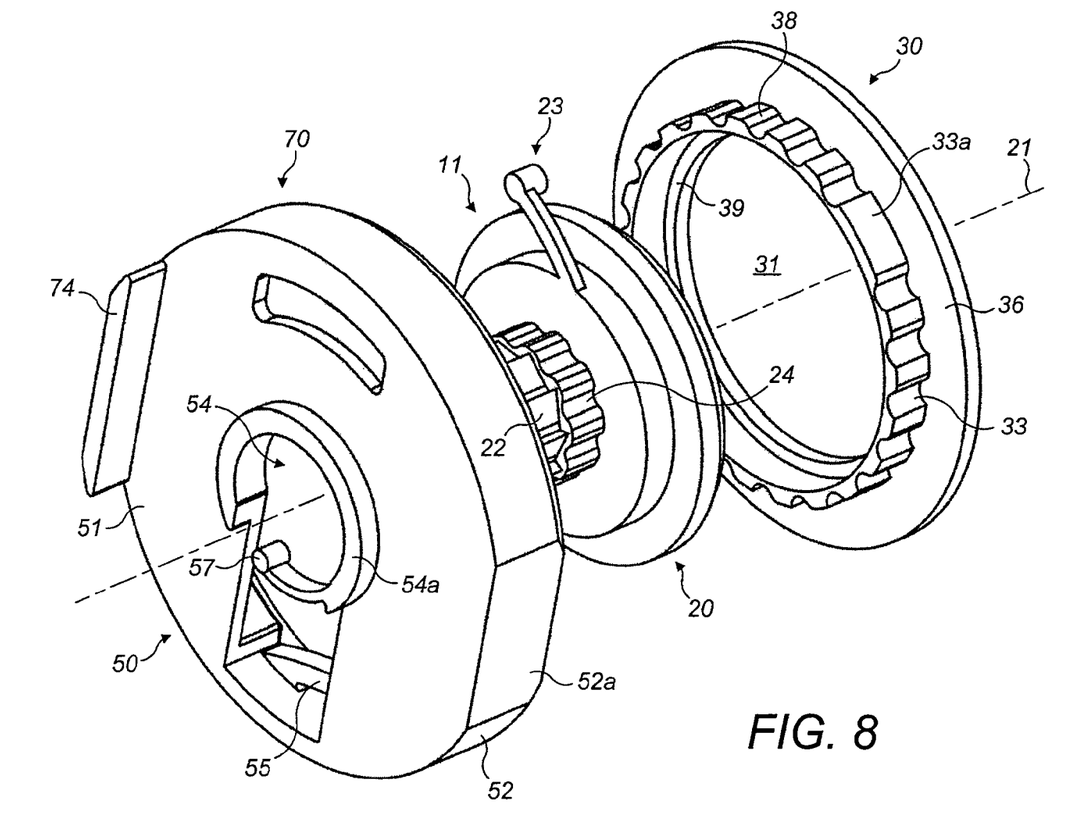
FIG. 8 is an exploded perspective view of the portion of the dose indicator device of FIG. 5.

The annular outer wheel 12, as shown in FIG. 8, has a generally annular body 30 which in use is rotatable about the longitudinal axis 21. The body 30 comprises an annular portion 38 a dependent flange 36. The annular body 30 defines a central aperture 31 which accommodates on assembly as described below a portion of the inner wheel 11. The flange 36 extends both radially outwards of the annular portion 38 and also for a distance radially inwardly of the annular portion 38 to define an annular shoulder 39 as shown in FIG. 8. A plurality of indexing teeth 33 are provided around an outer face of the annular portion 38. In the example shown 21 indexing teeth 33 are provided. As well as the indexing teeth 35, the outer face of the annular portion 38 is provided with a land 33a the function of which will be described below.

An outwardly-facing face 36a of the flange 36 and/or the end face 20a of the inner wheel 11 are provided with one or more indicia to provide information to a user of the pressurised metered dose inhaler 1 regarding the number of doses dispensed from the inhaler or remaining in the inhaler. For example, the indicia may comprise a set of increasing or decreasing numbers, a series of pictograms, a series of words or a band of changing colour—e.g. a band which changes from green to red around the circumference of the annular outer wheel 12.

Figure 3:
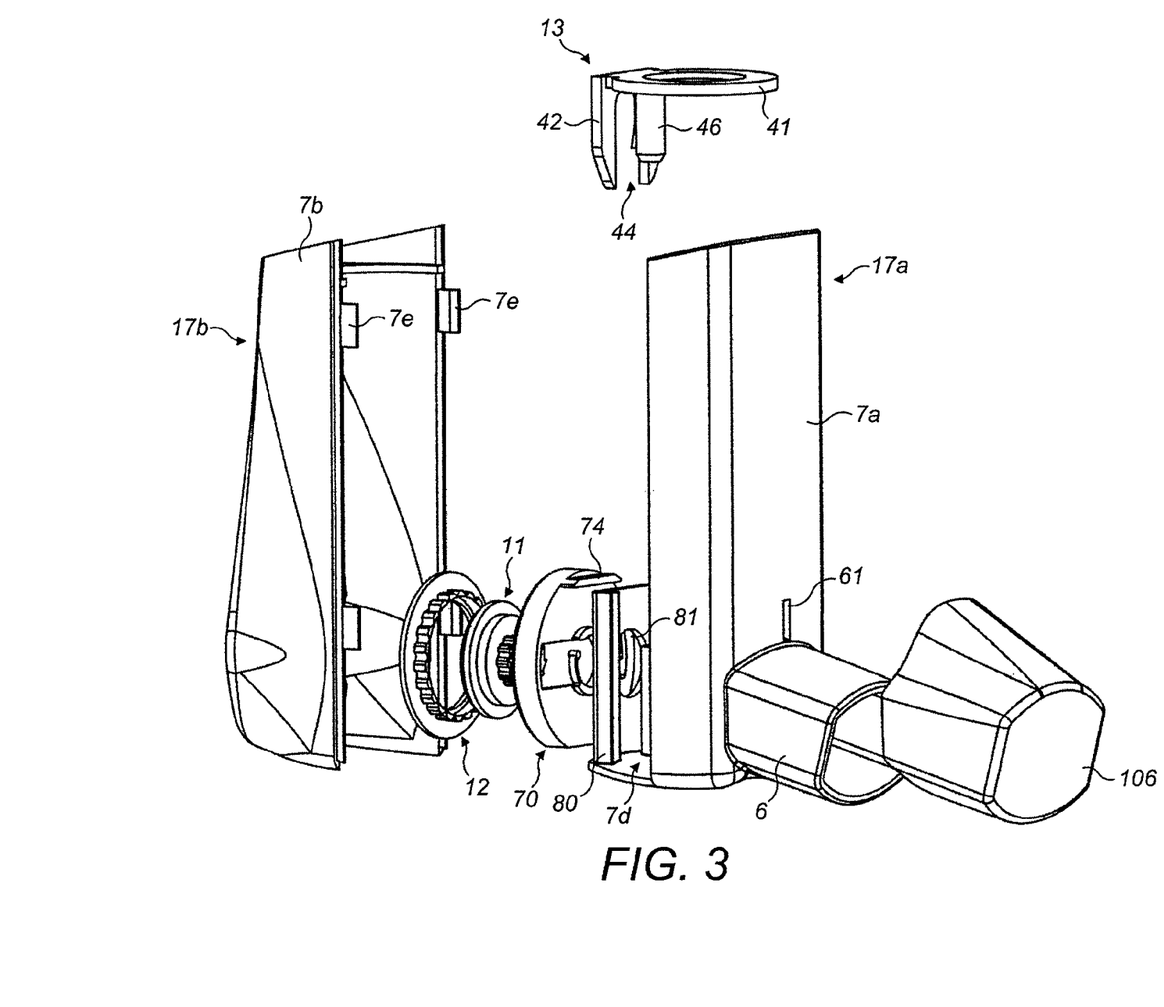
FIG. 3 is an exploded perspective view of the pressurised dispensing container of FIG. 1 from another angle.

As shown in FIGS. 2 to 4, the actuator member 13 comprises a yoke 41 at its upper end from which depend two legs 42 defining a channel 44 therebetween. An actuator drive arm 45 in the form of a flexible extension is provided on one of the legs 42 facing, and extending into, the channel 44. In use, as described below the actuator drive arm 45 drives the rotation of the inner wheel 11. Also depending from the yoke 41 is a plunger rod 46.

Figure 9:
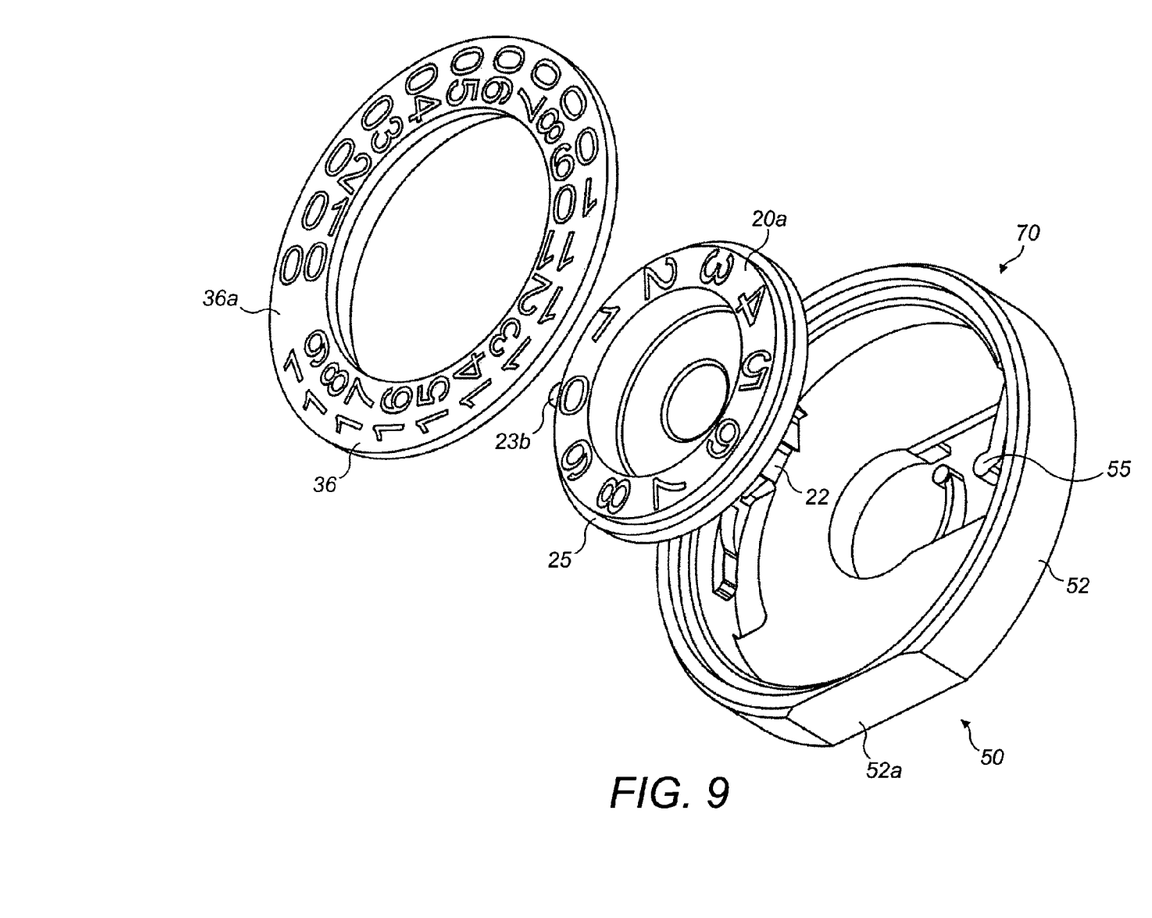
FIG. 9 is an exploded perspective view of the portion of the dose indicator device of FIG. 5 from another angle.

The cup-shaped housing 70 is shown most clearly in FIGS. 8 and 9. The cup-shaped housing 70 comprises a body 50 which has a generally disc-shaped planar portion 51 and a dependent rim 52 which is generally circular except for a flattened section 52a. A projection 74 located at one point of the periphery of the body 50 projects perpendicularly to the planar portion 51. The disc-shaped portion 51 of the body 50 comprises a centrally-located aperture 54 bounded by a rim 54a which, as described below, in use accommodates a portion of the inner wheel 11. A portion of the rim 54a is interrupted and in the gap is provided a first flexible restraining arm 57 in the form of a flexible arm portion which has a circular pin at its distal end. A second flexible restraining arm 55 that again has a circular formation at its distal end is provided on the inner face of the rim 52. Opposite the restraining arm 55 is provided on the inner face of the rim 52 a deflector 59 the function of which will be described below.

Figure 6:
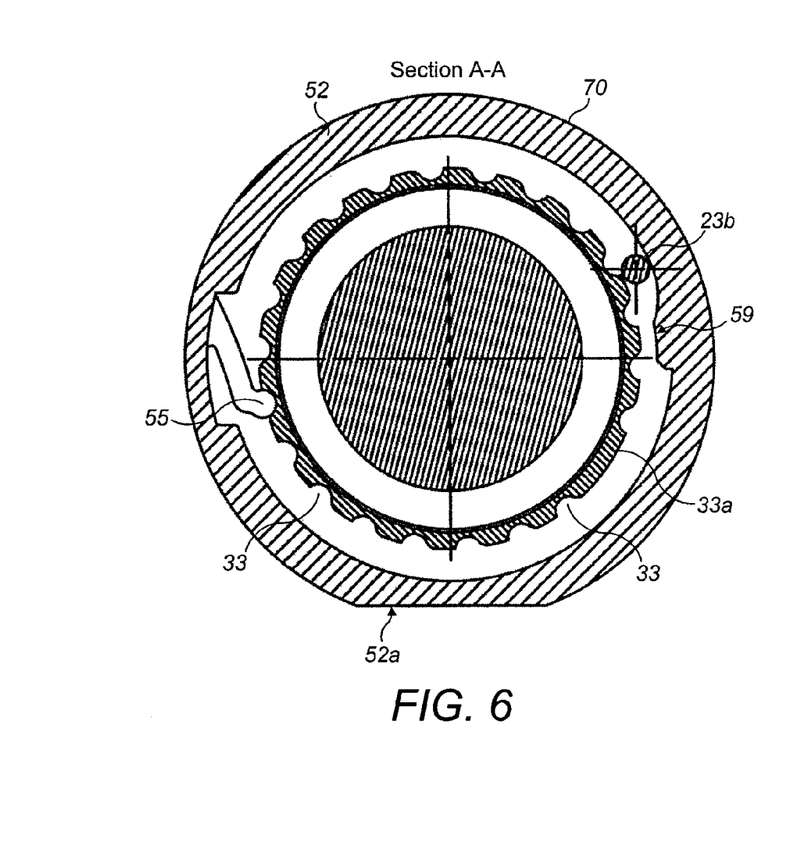
FIG. 6 is a cross-sectional view of the portion of the dose indicator device of FIG. 5.

To assemble the pressurised metered dose inhaler 1, the annular outer wheel 12, inner wheel 11 and cup-shaped housing 70 are first nested together. When nested the primary indexing teeth 22 of the inner wheel 11 project through the aperture 54 with the indentations 24 being aligned with and bearing against the inner face of the rim 54a. Also the peripheral rebate 25 of the inner wheel 11 engages against the shoulder 39 of the annular outer wheel 12. With the inner wheel 11 and annular outer wheel 12 nested together the pin 23b of the flexible drive arm 23 lies radially just outwards of the location of the indexing teeth 33 of the annular outer wheel 12 but extends in the direction of the longitudinal axis 21 to be in line with the plane of the indexing teeth 33 as shown in FIG. 6. As such, the arm portion 23a of the flexible drive arm 23 spans the annular portion 38. At the same time, the restraining arm 55 of the cup-shaped housing 70 is engaged with one of the indexing teeth 33. The flange 36 is fully received within the cavity of the cup-shaped housing 70. As such, a very compact arrangement is obtained as shown in FIG. 5 where the depth of the inner wheel 11 and annular outer wheel 12 are fully contained within the depth of the cup-shaped housing 70.

The nested annular outer wheel 12, inner wheel 11 and cup-shaped housing 70 are then inserted into the cavity 71a defined by the rim 71 of the rear case 17b. The rim 71 serves to locate the other components and prevent rotation of the cup-shaped housing 70 relative to the rear case 17b by virtue of the inter-engagement of the flattened sections 52a and 71b.

Next, the spring 15 is inserted into the bore of the tubular extension 10. The actuator member 13 is then inserted with the two legs 42 being slidingly received in the C-section channel 80. At the same time the plunger rod 46 is engaged in the open end of the bore of the tubular extension 10 so as to contact and rest on the upper end of the spring 15.

The front and rear cases 17a and 17b are then fastened together. Once fastened the cup-shaped housing 70 is abutted against the rear face of the C-section channel 80 such that the indexing teeth 22 of the inner wheel 1 project through the aperture 81 in the C-section channel 80 into alignment with the legs 42 and flexible drive arm 45 of the actuator member 13. The abutment prevents any of the components becoming disengaged from one another. In addition, when abutted the projection 74 of the cup-shaped housing spans across the top of the C-section channel 80 preventing the actuator member 13 from becoming detached from the C-section channel is the actuator housing is inverted.

A pressurised dispensing container 3 can now be inserted through the open end 7f of the tubular body 7 such that a leading face of a ferrule of the dispensing container 3 contacts the yoke 41 of the actuator member 13. The aperture in the middle of the yoke 41 accommodates the valve stem to enable it to project beyond the yoke 41 into engagement with the stem block 8. The action of the spring 15 on the base of the plunger rod 46 ensures that in the rest position, the yoke 41 is held in face to face contact with the ferrule of the dispensing container 3.

Figure 7:
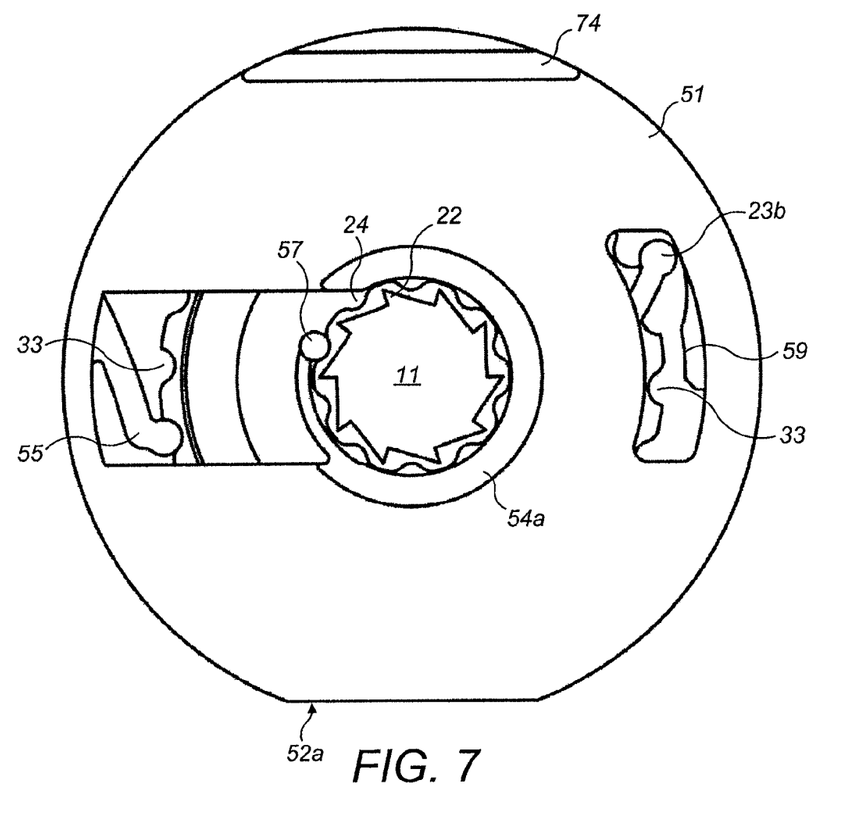
FIG. 7 is an end elevation of the portion of the dose indicator device of FIG. 5.

FIGS. 6 and 7 illustrate the relative positions of the inner wheel 11, annular outer wheel 12 and cup-shaped housing 70 at the rest position. At rest, the distal end of the actuator drive arm 45 is out of contact with the primary indexing teeth 22 of the inner wheel 11. Also, in this rest position, the first flexible restraining arm 57 is engaged with one of the indentations 24 of the inner wheel 11 and the second flexible restraining arm 55 is engaged with one of the indentations 33 of the annular outer wheel 12. The purpose of the first and second flexible restraining arms is to restrain inadvertent rotation in either direction of either the inner wheel 11 or the annular outer wheel 12 other than when the components are being actively driven on actuation of the dispensing container 3 as will be described below. In other words, the action of the flexible restraining arms helps to prevent actuation of the dose indicator device 9 if the device is dropped, shaken or knocked.

In operation, as is normal for a pressurised metered dose inhaler, the dispensing container 3 is depressed relative to the housing 2 such that the canister 4 moves downwardly within tubular body 7 towards the stem block 8 to actuate the valve.

On actuation of dispensing container 3, downward movement of the canister 4 and valve 5 within the tubular body 7 causes the actuator member 13 to be moved downwardly within the tubular body 7 so as to compress spring 15 due to contact between the yoke 41 and the ferrule. At the same time, the legs 42 and thus the actuator drive arm 45 are moved downwardly relative to the C-shaped channel 80 and the inner wheel 11. This brings the distal end of the actuator drive arm 45 into contact with one of the primary indexing teeth 22 and onward movement of the actuator arm 45 causes the inner wheel 11 to be rotated by one increment. Rotation of the inner wheel 11 is accommodated by radially-outward flexing of the first flexible restraining arm 57 such that the circular formation at the distal end of the first flexible restraining arm 57 is displaced from its initial indentation 24 and then re-engages into a neighbouring indentation 24 associated with a neighbouring primary indexing tooth 22 to that being engaged by the actuator drive arm 45. During rotation of the inner wheel 11 the pin 23b moves around the annular gap between the teeth 33 of the annular outer wheel 12 and the rim 52 of the cup-shaped housing 70. This movement of the pin 23b does not interact with the teeth 33 until contact with the deflector 59 as described below.

On release of the dispensing container 3, the dispensing container 3 moves back upwardly within the tubular body 7 under the internal spring bias of the valve 5. This upward movement allows the actuator member 13 to move back upwardly within tubular body 7 under action of spring 15. This causes in turn the legs 42 and yoke 41 to move back upwardly relative to the inner wheel 11 back into the at rest position. Depending on the number of primary indexing teeth 22 and their relative spacing, this upward movement may be accommodated by the actuator drive arm 45 flexing and riding back over the neighbouring primary indexing tooth 22. In such a situation, the engagement of the first flexible restraining arm 57 in the indentation 24 prevents any back rotation of the inner wheel 11.

Thus, on each actuation of the dispensing container 3, the inner wheel 11 is rotated by one increment. Successive actuations of the dispensing container 3 continue to rotate the inner wheel 11 until the point that the pin 23b moves round into engagement with the deflector 59. At this point, on actuation of the dispensing container 3, the inner wheel 11 is rotated as described above and at the same time the pin 23b is deflected radially inwardly into engagement with one of the teeth 33 of the annular outer ring such that the annular outer wheel 12 is rotated by one increment. Advantageously, no transmission cog is required to transfer the motive force from the inner wheel 11 to the annular outer wheel 12. As with the movement of the inner wheel 11, the rotation of the annular outer wheel 12 is accommodated by radially-outward flexing of the second flexible restraining arm 55 to move the circular formation at the distal end of the second flexible restraining arm from its tooth 33 on to a neighbouring tooth 33. Both the inner wheel 11 and the annular outer wheel 12 rotate in the same sense, which may be designed to be either clockwise or anti-clockwise.

In this way, reciprocal longitudinal movement of the dispensing container 3 can be used to create rotational movement of the inner wheel 11 and the annular outer wheel 12 to change display of dosage indicia provided on the inner wheel 11 and or annular outer wheel 12.

At the end of life of the pack the rotation of the inner wheel 11 will bring the pin 23b into contact with the land 33a of the annular outer wheel 12. At this point further rotation of the annular outer wheel 12 is prevented since the pin 23b is unable to engage with a tooth 33 to rotate the annular outer wheel 12.

When not in use the dust cap 106 can be placed on the mouthpiece 6. The tang 161 projects through the lock-out aperture 61 to prevent actuation of the counter by contacting and blocking downward movement of the yoke 41.

Figure 10:
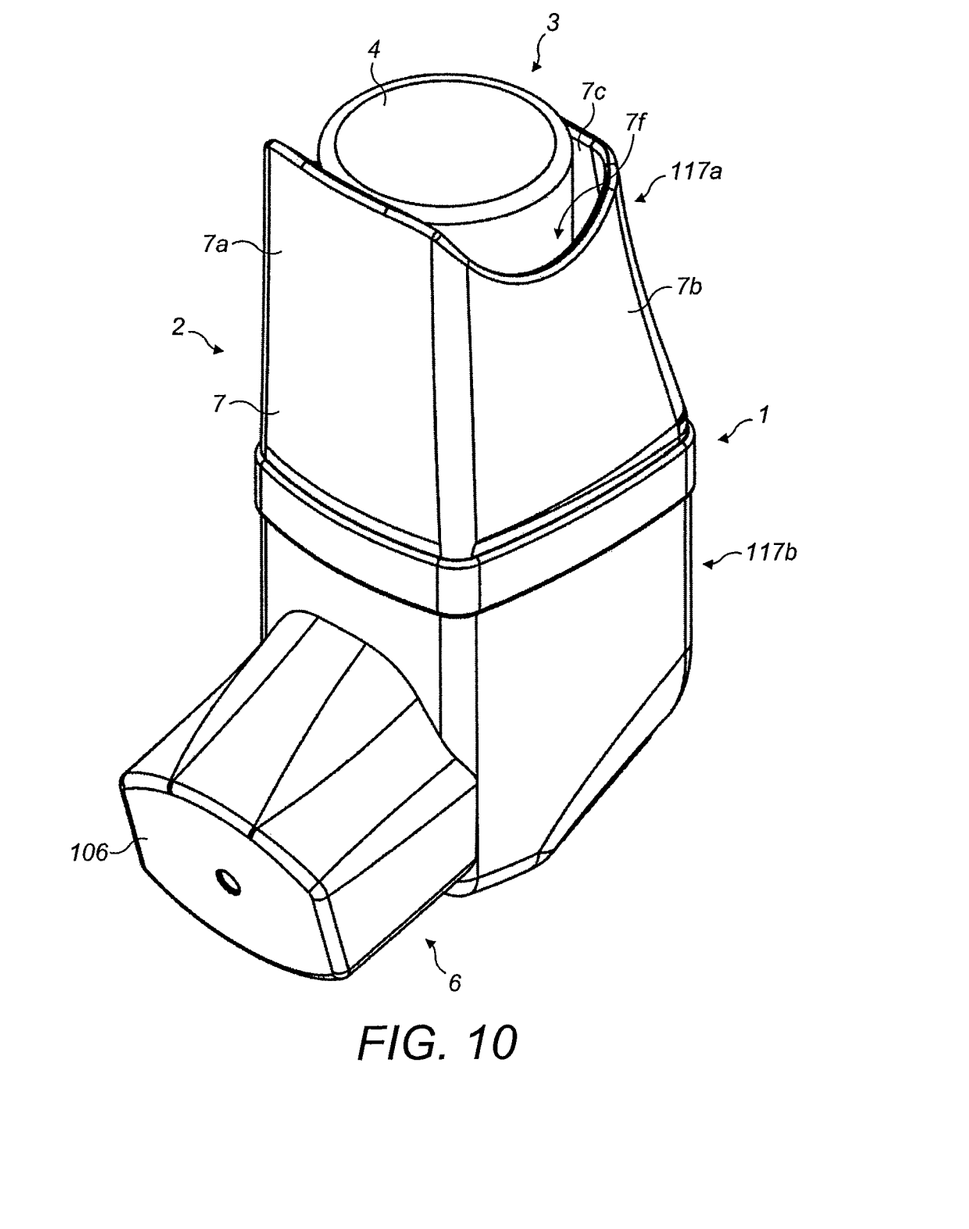
FIG. 10 is a perspective view of another embodiment of pressurised metered dose inhaler comprising a dose indicator device according to the present disclosure and including a pressurised dispensing container.
Figure 11:
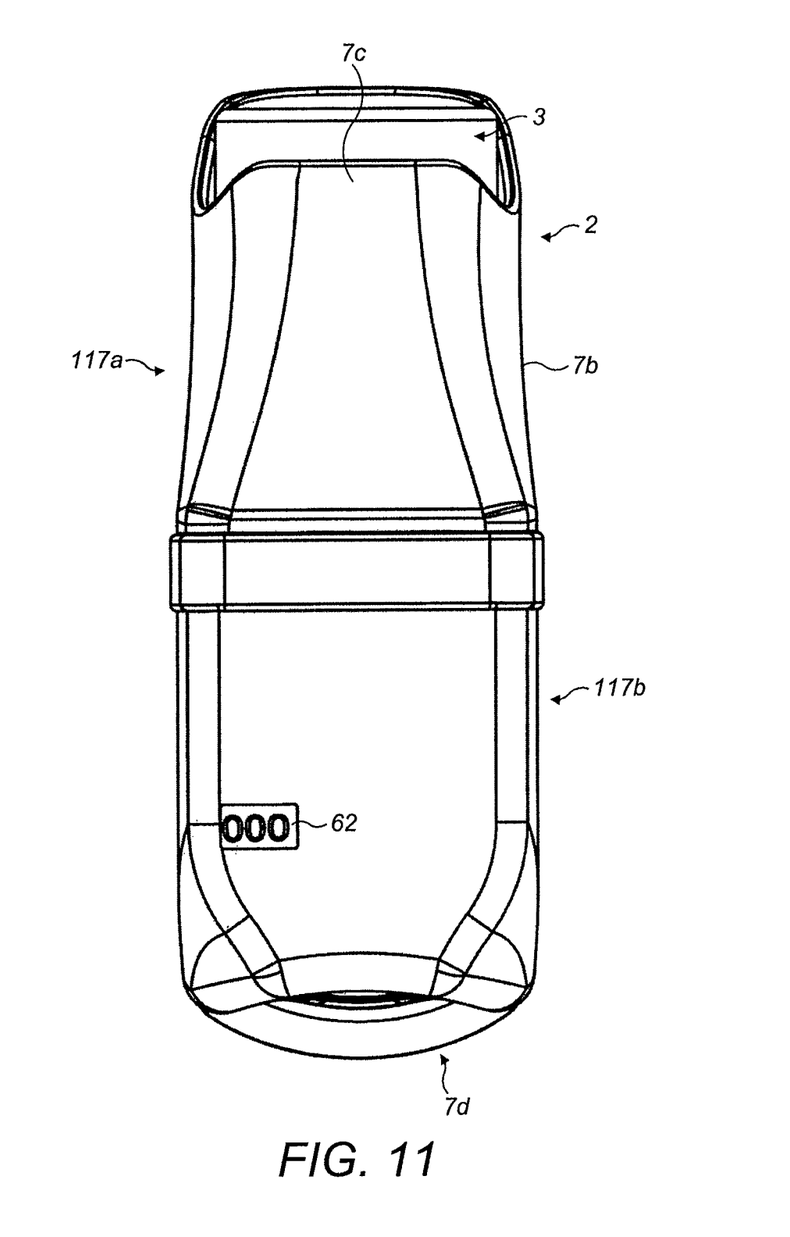
FIG. 11 is a rear view of the pressurised metered dose inhaler of FIG. 10.
Figure 12:
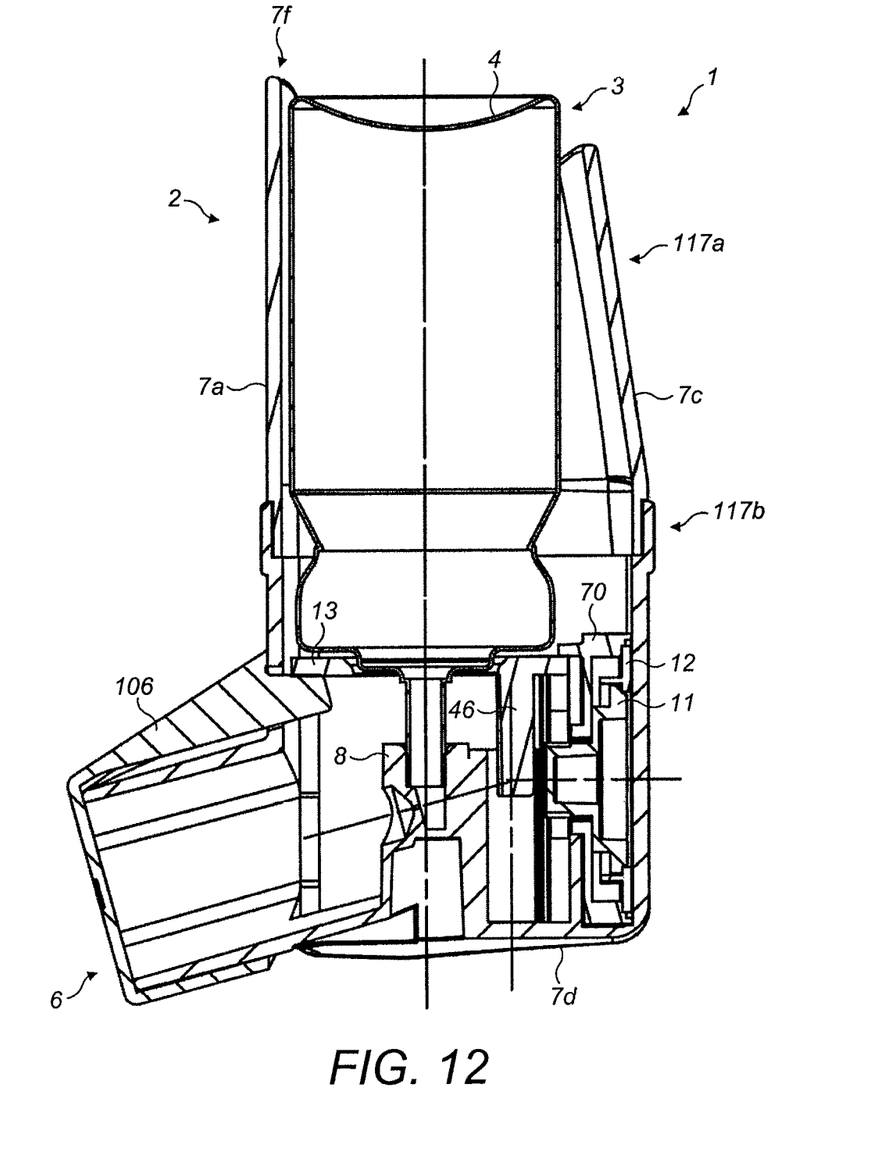
FIG. 12 is a cross-sectional view of the pressurised metered dose inhaler of FIG. 10.

FIGS. 10 to 12 show another embodiment of pressurised metered dose inhaler 1 according to the present disclosure. The structure and function of this embodiment is similar to that of the embodiment of FIGS. 1 to 9 and in the following only the differences will be described in detail. Equivalent features have been referenced using equivalent reference numerals.

The tubular body 7 of the actuator housing 2 of this embodiment is formed from two mouldings comprising a top case 117*a* and a bottom case 117*b*. The bottom case 117*b* fully defines the mouthpiece 6, the stem block 8 and the base 7*d* of the actuator housing. In addition, the C-section channel 80 and the tubular extension 10 form part of the bottom case 117*b*. As can be seen in FIG. 12, the bottom case 117*b* fully houses the dose indicator device 9. The top case 117*a* in this embodiment shields the majority of the body of the pressurised dispensing container 3. The top case 117*a* may be formed from a transparent or translucent material to allow markings or writing on the pressurised dispensing container 3 to be read without the need to remove the container from the actuator housing 2.

The top and bottom cases 117*a*, 117*b* may be snap-fit together by means of formations on each casing.

As before, the pressurised dispensing container 3 is inserted into the actuator housing 2 through the open upper end 7*f*—in this embodiment fully defined by the top case 117*a*.

Operation of the pressurised metered dose inhaler 1, including actuation of the dose indicator device 9 is the same as in the previous embodiment.

The invention claimed is:

1. A dose indicator device for a pressurized metered dose inhaler comprising:
   an inner wheel, an annular outer wheel, an actuator and a housing;
   the inner wheel comprising a plurality of primary indexing teeth and a flexible drive arm;
   the annular outer wheel comprising a plurality of secondary indexing teeth on an outer face of the annular outer wheel;
   the inner wheel and the annular outer wheel being located at least partially within the housing such that the inner wheel and the annular outer wheel are rotatable about a common longitudinal axis of rotation;
   the actuator being movable in a plane perpendicular to the longitudinal axis of rotation to engage the primary indexing teeth of the inner wheel to rotate the inner wheel; the housing being fixed relative to the longitudinal axis of rotation and comprising a deflector;
   the deflector being configured such that, on rotation of the inner wheel, the flexible drive arm is intermittently deflected by the deflector and is thereby brought into contact with the secondary indexing teeth so as to rotate the annular outer wheel about the longitudinal axis of rotation;
   wherein the housing further comprises a first flexible restraint which engages the inner wheel to restrain rotation of the inner wheel when not being rotated by the actuator and a second flexible restraint which engages the annular outer wheel to restrain rotation of the annular outer wheel when not being rotated by the inner wheel; and wherein the second flexible restraint is engageable with the secondary indexing teeth of the annular outer wheel;
   wherein the actuator is provided on an actuator member, said actuator member being movable by a dispensing container of a pressurized metered dose inhaler into an indexing position on actuation of the pressurized metered dose inhaler to engage the actuator with the primary indexing teeth of the inner wheel to rotate the inner wheel; and
   wherein said actuator member is biased away from the indexing position such that the actuator is disengaged from the primary indexing teeth when the pressurized metered dose inhaler is in a non-dispensing position.

2. A dose indicator device as claimed in claim 1 wherein the inner wheel is at least partially nested within a longitudinal extent of the annular outer wheel.

3. A dose indicator device as claimed in claim 1 wherein the deflector is configured such that, on rotation of the inner wheel, the flexible drive arm is intermittently deflected by the deflector inwardly towards the longitudinal axis of rotation.

4. A dose indicator device as claimed in claim 3 wherein a proximal end of the flexible drive arm of the inner wheel is located closer to the longitudinal axis of rotation than the secondary indexing teeth and a distal end of the flexible drive arm is located further from the longitudinal axis of rotation than the secondary indexing teeth when not in contact with the deflector.

5. A dose indicator device as claimed in claim 1 wherein the inner wheel comprises a plurality of indentations on an outer face of the inner wheel which are engageable by the first flexible restraint.

6. A dose indicator device as claimed in claim 5 wherein the plurality of indentations are located circumferentially around the inner wheel with the primary indexing teeth located to one side of the plurality of indentations.

7. A dose indicator device as claimed in claim 1 wherein the housing comprises a mounting aperture for the inner wheel enabling the inner wheel to rotate therein relative to the housing.

8. A dose indicator device as claimed in claim 7 wherein the inner wheel comprises a plurality of indentations on an outer face of the inner wheel which are engageable by the first flexible restraint and wherein the plurality of indentations form a bearing surface of the inner wheel in the mounting aperture.

9. A dose indicator device as claimed in claim 8 wherein a portion of a boundary of the mounting aperture comprises the first flexible restraint which is engageable with the plurality of indentations of the inner wheel to restrain rotation of the inner wheel when not being rotated by the actuator.

10. A dose indicator device as claimed in claim 1 wherein the inner wheel and the annular outer wheel have a gear ratio such that for every 10 incremental rotations of the inner wheel the annular outer wheel is incrementally rotated once.

11. A dose indicator device as claimed in claim 1 wherein the housing comprises a first housing part which is engageable with a wall portion of an actuator housing of a pressurized metered dose inhaler to define a housing enclosure containing the inner wheel and the annular outer wheel.

12. A dose indicator device as claimed in claim 11 wherein the first housing part comprises the deflector.

13. A dose indicator device as claimed in claim 1 wherein the inner wheel and/or the annular outer wheel comprise dosage indicia.

14. A dose indicator device as claimed in claim 13 wherein the dosage indicia are provided on an end face of the inner wheel and/or the annular outer wheel, the end faces being perpendicular to the longitudinal axis of rotation.

15. A pressurized metered dose inhaler comprising an actuator housing, a pressurized dispensing container received in the actuator housing and a dose indicator device as claimed in claim 1.

16. A pressurized metered dose inhaler as claimed in claim 15 comprising a housing enclosure containing the inner wheel and the annular outer wheel, the housing enclosure being defined by a first housing part of the dose indicator device and a wall portion of the actuator housing.

17. A pressurized metered dose inhaler as claimed in claim 16 wherein the wall portion comprises a rear wall of the actuator housing such that the housing enclosure is located between a stem block and the rear wall of the actuator housing.

18. A pressurized metered dose inhaler as claimed in claim 15 comprising a front case and a rear case.

19. A pressurized metered dose inhaler as claimed in claim 18 wherein the front case comprises a dispensing orifice and a stem block.

20. A pressurized metered dose inhaler as claimed in claim 18 further comprising a housing enclosure containing the inner wheel and the annular outer wheel of the dose indicator device; the housing enclosure being defined by a first housing part of the dose indicator device and a wall portion of the rear case of the actuator housing.

21. A pressurized metered dose inhaler as claimed in claim 15 comprising a top case and a bottom case.

22. A pressurized metered dose inhaler as claimed in claim 21 wherein the bottom case comprises a dispensing orifice and a stem block.

23. A pressurized metered dose inhaler as claimed in claim 21 further comprising a housing enclosure containing the inner wheel and the annular outer wheel of the dose indicator device; the housing enclosure being defined by a first housing part of the dose indicator device and a wall portion of the bottom case of the actuator housing.

24. A pressurized metered dose inhaler as claimed in claim 15 further comprising a window in the actuator housing for viewing the inner wheel and/or the annular outer wheel therethrough.

25. A pressurized metered dose inhaler as claimed in claim 24 wherein the window is sized so as only to show the annular outer wheel and to obscure view of the inner wheel.

* * * * *